(12) United States Patent
Ylostalo et al.

(10) Patent No.: US 9,782,095 B2
(45) Date of Patent: Oct. 10, 2017

(54) SINGLE-USE BIOMEDICAL SENSORS

(75) Inventors: Antti Kustaa Antipas Ylostalo, Helsinki (FI); Juha Petri Virtanen, Helsinki (FI)

(73) Assignee: GENERAL ELECTRIC COMPANY, Schenectady, NY (US)

(*) Notice: Subject to any disclaimer, the term of this patent is extended or adjusted under 35 U.S.C. 154(b) by 166 days.

(21) Appl. No.: 13/328,035

(22) Filed: Dec. 16, 2011

(65) Prior Publication Data

US 2012/0209102 A1 Aug. 16, 2012

(30) Foreign Application Priority Data

Dec. 20, 2010 (EP) .................................. 10195886

(51) Int. Cl.
*A61B 5/04* (2006.01)
*A61B 5/0408* (2006.01)
*A61B 5/00* (2006.01)
*A61B 5/0478* (2006.01)
*A61B 5/0492* (2006.01)

(52) U.S. Cl.
CPC .......... *A61B 5/0408* (2013.01); *A61B 5/0006* (2013.01); *A61B 5/0478* (2013.01); *A61B 5/6833* (2013.01); *A61B 5/04087* (2013.01); *A61B 5/0492* (2013.01); *A61B 2560/0412* (2013.01); *A61B 2562/125* (2013.01); *A61B 2562/164* (2013.01)

(58) Field of Classification Search
CPC ...... A61N 1/0492; A61N 1/08; A61N 1/0472; A61N 1/365; A61N 1/37; A61N 1/00; A61N 1/375; A61N 1/3752; A61L 35/0205; A61L 35/0452; A61L 35/0006; A61L 35/02; A61L 35/0422

USPC ....... 600/372, 382, 384, 386, 388, 391–393, 600/508–509
See application file for complete search history.

(56) References Cited

U.S. PATENT DOCUMENTS

| 3,943,937 | A | * | 3/1976 | King | A61N 1/375 429/57 |
| 4,270,544 | A | * | 6/1981 | Gilden et al. | 600/392 |
| 6,561,978 | B1 | * | 5/2003 | Conn | A61B 5/0031 600/309 |

(Continued)

FOREIGN PATENT DOCUMENTS

| CN | 1659726 A | 8/2005 |
| CN | 101631587 A | 1/2010 |
| WO | 2008005016 A1 | 1/2008 |

OTHER PUBLICATIONS

Eugene Avallone et al. Marks' Standard Handbook for Mechanical Engineers 11th Edition. McGraw-Hill Professional, 2006.*

(Continued)

*Primary Examiner* — Joseph Stoklosa
*Assistant Examiner* — Brian M Antiskay

(57) ABSTRACT

A disposable self-powered biomedical sensor comprises a printed wet electrode on a substrate sheet. The wet electrode is provided with an electrolyte element to enhance the electrical contact with a surface to be measured. Moreover, a printed battery encapsulated in a hermetically sealed compartment is provided on the substrate sheet. The disposable self-powered sensor can be stored within an enclosure or a package which provides a proper atmosphere to prevent the drying of the electrolyte and prolong the shelf life of the sensors.

19 Claims, 2 Drawing Sheets

(56) References Cited

U.S. PATENT DOCUMENTS

| | | | |
|---|---|---|---|
| 7,447,534 B1* | 11/2008 | Kingsley et al. | 600/372 |
| 2005/0131288 A1 | 6/2005 | Turner et al. | |
| 2007/0088227 A1* | 4/2007 | Nishimura | A61B 5/04085 600/391 |
| 2007/0255153 A1* | 11/2007 | Kumar | A61B 5/0006 600/515 |
| 2009/0076363 A1* | 3/2009 | Bly | A61B 5/4875 600/372 |
| 2009/0076364 A1* | 3/2009 | Libbus et al. | 600/391 |
| 2012/0089000 A1* | 4/2012 | Bishay | A61B 5/02438 600/391 |
| 2012/0089037 A1* | 4/2012 | Bishay | A61B 5/0404 600/509 |

OTHER PUBLICATIONS

Wong, A.C.W, et al. "Sensium: an ultra-low-power wireless body sensor network platform: Design & application challenges", 2009 Annual International Conference of the IEEE Engineering and Medicine and Biology Society: EMBC 2009; Minneapolis, Minnesota, USA, Sep. 3-6, 2009, IEEE, Piscataway, NJ, USA, Sep. 3, 2009, pp. 6576-6579.

Unofficial translation of Chinese Search Report from corresponding CN Patent Application No. 201110463147.0 dated May 11, 2015.

* cited by examiner

SINGLE-USE BIOMEDICAL SENSORS

BACKGROUND OF THE INVENTION

Field of the Invention

The disclosure relates generally to electrodes for obtaining biosignals from a recording surface, for example a skin of a subject.

Description of the Prior Art

When monitoring the vital signs or other physiological parameters of hospitalized patients, sensors are attached on patients' skin or catheters are inserted either into natural openings of the body or catheters are pierced through the skin. The common practice is to connect these sensors with electrically or optically conductive cables to measurement instruments. The instrument may reside either on bedside (e.g. multi-parameter patient monitors in operating room (OR) or in intensive care unit (ICU)) or it may be a relatively small box carried by the patient (e.g. ECG telemetry).

Recent technological development has made it possible to build battery-operated sensors, which include means for performing the actual measurement, converting the measured signals into digital format, and transmitting wirelessly the measurement data and/or calculated parameters to a host device. These devices are referred to as wireless sensors.

Wireless sensors provide obvious benefits for both caregivers and patients. The so-called 'cable clutter' has been recognized as one of the biggest issues in the care process of high-acuity patients. There are lots of cables in the hospitals that also create issues with infections and the usability. By using wireless sensors one can reduce the amount of cables used in a hospital and improve the usability of the different parameters and the total care process. It is not necessary to remove all the cables, but a significant improvement would be achieved by removing only a moderate number of leads or wires. This is because the tendency to tangle up increases disproportionally with the number of cables. The patient group, which would benefit most from the wireless sensors, is low-acuity patients. Being not physically tied to the patient monitor with lead wires, they are free to move around, like visiting the bathroom without assistance. Also in case of a small patient monitor carried by the patient, wireless sensors offer better reliability and are more comfortable for the patient.

Another aspect supporting the use of disposable sensors in hospital environment is the infection control, which has become a big issue. The term "disposable" as used herein refers to a single-use sensor which is used once and then disposed. Totally disposable sensors would make infection control easier. They would also streamline the care process by eliminating the need for cleaning the sensors. If one is able to use disposable single-patient-use sensors, it prevents the spreading of infections and cross contamination inside the hospital. This also improves the care process by saving time and money.

There are several disposable sensors available in the market such as a depth-of-anesthesia sensor, ECG electrodes, etc. There are also some wireless parameters available in the markets. Most of the wireless parameters are reusable or disposable with changeable or rechargeable battery. All of these variations require charging or special handling of the batteries. The also require special installation when starting to use the parameter because the battery needs to be added to the sensor separately. Difficult maintenance and high cost related to batteries has been the key factor in preventing wireless sensors from becoming widely accepted. Moreover, typically the batteries used needs to be recycled. In order to gain wide acceptance for the wireless sensors, the battery replacement cycle should match the hospital's daily routine and the disposed batteries and sensors should require no special handling Disposable sensors that contain electrodes (such as ECG, EEG etc. . . . ) has limited shelf life for several reasons. Electrodes for measuring biosignals from a recording surface, for example a skin of a patient may be generally classified into dry electrodes or wet electrodes depending on the presence of an electrolyte on the surface attached to the skin. Dry electrodes are mainly applied to the skin using an elastic band. An example of a dry electrode is heart rate meter belt used in sports medicine. On the other hand, wet electrodes may be attached to the skin using a conductive liquid or solid gel to provide a continuous conductive path between the recording surface and the electrode sensing element. Conductive gels may contain a salt, such as KCl or NaCl, in order to achieve electrical current flow. The preferred gel is one with a high salt content, since such a gel produces a better conductor than that obtained when using a gel with low salt content. In addition, the use of a high salt content typically requires less skin abrasion at the time of application to reduce the impedance of the skin-electrode interface after subsequent electrode application. Consequently, biosignal measurement sensor electrodes with high salt content traditionally may have a limited shelf life (maximum storage time prior to use), for example, due to drying of the gel in the electrodes, and also due to the changes that may take place in the sensor materials. Wet gel electrodes provide better contact that dry electrodes: the contact impedance is lower and the signal bandwidth extends to lower frequencies. This is why dry electrodes are typically used in limited applications, such as heart rate measurement, whereas wet gel electrodes are used in diagnostic ECG, where various features of the signal are analysed.

For a long-term storage, e.g. up to about 12 months, wet sensors or sensor electrodes may be stored within an enclosure or a package, which provides a proper atmosphere to prevent the drying of the gel. For example, a pouch laminated with moisture and UV-proof materials, such as aluminum, may be used to prevent the drying of the gel. As a result there is an atmosphere inside the pouch where humidity may be about 99%. There may be salt (Chloride) present inside the pouch, since the electrolyte gels contains typically KCl or NaCl to enable good signal between the electrode and the tissue. Thus, the humidity and the existence of the salt inside the pouch creates an atmosphere which is really harmful for several materials. This atmosphere corrodes many materials and chlorides or oxidizes them and it requires special attention to the material selections of the sensor.

BRIEF SUMMARY OF THE INVENTION

An aspect of the present invention provides a self-powered single-use biomedical sensor comprising a conductive electrolyte material.

Another aspect of the present invention provides a self-powered wireless biomedical sensor comprising a conductive electrolyte material and offering long shelf life.

A still another aspect of the present invention provides a self-powered biomedical sensor comprising a conductive electrolyte material and withstanding a high humidity and saline storage environment.

An aspect of the invention is a biomedical sensor, comprising: a substrate sheet, at least one printed electrode on said substrate sheet, the at least one electrode being provided with an electrolyte element to enhance the electrical contact with a surface to be measured, and at least one battery encapsulated in a hermetically sealed compartment on said substrate sheet.

Another aspect of the invention is a hermetically sealed package containing a biomedical sensor that comprises: a substrate sheet, at least one printed electrode on said substrate sheet, the at least one electrode being provided with an electrolyte element to enhance the electrical contact with a surface to be measured, and at least one disposable printed battery encapsulated in a hermetically sealed compartment on said substrate sheet.

BRIEF DESCRIPTION OF THE DRAWINGS

The following exemplary embodiments will be described in greater detail with reference to the attached drawings, in which.

DETAILED DESCRIPTION OF THE INVENTION

An electrode for measuring biosignals from a recording surface, for example a skin of a patient, may be called as a 'wet' electrode in presence of an electrolyte on the contact surface attached to the skin. A 'wet' electrode may be attached to the skin using a conductive liquid, hydrogel or solid gel, e.g. electrolyte gel, to improve the electrical conductivity between the recording surface and the electrode sensing element, such as a silver/silver chloride (Ag/AgCl) electrode layer. Typical components of a conductive gel may include water (which acts as the solvent), water-soluble monomers which crosslink to give structure to the gel and which may also provide skin adhesion, humectant materials which reduce the dryout characteristics of the conductive gel, and electrolytes or salts, such as sodium chloride (NaCl) or potassium chloride (KCl) dissolved in water, which provide the ionic conductivity. One advantage of conductive gels over other conductive electrolytes is that they can be removed cleanly from the skin without leaving a residue.

Figure 1:
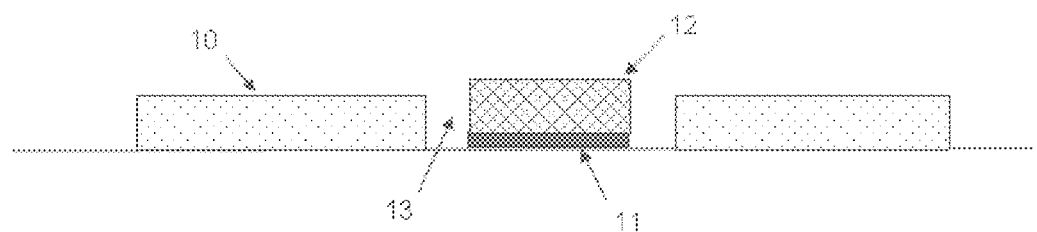
FIG. 1 illustrates an example of a prior art biomedical sensor.
Figure 2:
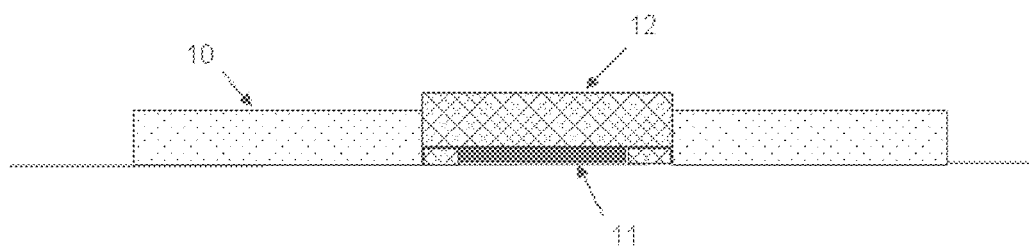
FIG. 2 illustrates another example of a prior art biomedical sensor.

FIG. 1 illustrates, in a side view, an example of a prior art biomedical sensor. The exemplary sensor may include a planar substrate (e.g. a film of non-conducting material, such as plastic), a conductive electrode layer 11 (e.g. silver (Ag) that is chloridised chemically with gel, silver/silver chloride (Ag/AgCl), a gel-carrying element 12 (such as a sponge soaked with a conductive gel) overlaying the conductive electrode layer, and an adhesive layer 10 (e.g. an adhesive foam material) surrounding the gel-carrying element 12 (in the same planar plane) for attaching the electrode to living tissue, for example human forehead or chest. The surrounding adhesive layer 10 may be spaced apart 13 from the gel-carrying element 12. FIG. 2 illustrates, in a side view, another example of a biomedical sensor. The exemplary electrode may include a planar substrate (e.g. a film of non-conducting material, such as plastic), a conductive electrode layer 11 (e.g. silver (Ag), silver/silver chloride (Ag, AgCl), a conductive gel 14 in a solid form ("a solid gel") overlaying the conductive electrode layer 11, and an adhesive layer 10 (e.g. an adhesive foam layer) surrounding the solid gel (in the same planar plane) for attaching the electrode to living tissue, for example human forehead or chest. In both examples, the conductive electrode layer 11 may contact the gel element 12 or 14 on one side (top side in FIGS. 1 and 2), and conducting traces (e.g. strips of conductive material provided on the substrate (not shown)) on the other side (bottom side in FIGS. 1 and 2). The electrode layer 11 is the interface at which ionic conduction through the conductive gel changes to electronic conduction to a monitoring/recording device. The traces, which may be printed or etched, for example, provide electrical connection between the electrode and an associated electronic circuit in the biomedical sensor patch, or via cables to the nearby monitoring device. The traces may also be printed, Ag, or Cu, for example. There may be a single electrode or electrode arrays containing multiple electrodes on the same substrate.

It should be appreciated that the biomedical sensors illustrated above are merely examples of sensors that use a conductive liquid, hydrogel or solid gel, commonly referred to as a conductive electrolyte or gel herein, to improve the electrical conductivity. Embodiments of the invention are not intended to be restricted to any specific sensor type but are applicable to any type of biomedical sensor that use any appropriate electrolyte, such as conductive gel, that must be protected from drying and that create a harmful high-humidity environment. GE Healthcare's Inc's depth-of-anesthesia sensor is a good example of a printed sheet sensor. It contains a substrate, conductive traces, conductive barrier layer and dielectric layer printed with screen-printing, flexoprinting or any other equivalent process. It also contains electrolyte get to enable biosignal measurement from living tissue. There are also various other sensors manufactured with similar technologies in the market.

"Wet" sensors with an electrolyte on the contact surface may be stored within an enclosure or a package which provides a proper atmosphere to prevent the drying of the electrolyte and prolong the shelf life of the sensors. The humidity (up to 99%) and the existence of the salt chloride (from the electrolyte) the sealed humidity-impermeable enclosure or package may create an atmosphere which is realty harmful for several materials. This atmosphere corrodes many materials and chlorides or oxidizes them and it requires special attention to the material selections of the sensor.

Soft batteries, such as printed batteries are manufactured using methods to create them disposable. These batteries do not contain any environmentally hazardous materials and can be disposed with the sensors without any special handling, such as circulation of batteries. This creates limitations on the material selections. Materials of the printed batteries can not be changed to stand the high humidity and corroding atmosphere. A typical packaging solution for the soft batteries is to use plastic or paper based electrically non-conductive material in making the package. Using of paper based package is not an option in the high humidity environment because the humidity and the salt would then absorb to the paper and short circuit the battery terminals. Some types of printed batteries may include wet electrolytes and they may be sealed within a plastic sheathing film to prevent liquid evaporation, and are therefore closed electrochemical cells. Being closed cells, these batteries may tend to swell upon storage due to undesirable gas formed within the battery.

Embodiments of the invention provide a disposable "wet" self-powered biomedical sensor comprising a conductive electrolyte material, withstanding a high humidity and saline storage environment, white allowing use of environmentally non-hazard materials in a battery such that no special handling is required at disposal of the sensor. A disposable battery is provided in a hermetically sealed compartment on the sensor structure, such that the unified battery-electrode combination can be stored within the same package or enclosure, such as within the same pouch, having an internal atmosphere with high humidity level, even up to about 99% and saline content since pouch contains electrolyte gel. As a result, a disposable "wet" self-powered biomedical sensor is provided that offers a long shelf life, e.g. a shelf life of the order of 6-12 months or more.

An aspect of the invention is to cover a printed disposable battery on the sensor with a humidity-blocking material so as to make the battery tolerant for humidity and saline atmosphere wherein the sensor is stored.

There are several methods to cover the battery to make it tolerant for humidity and saline atmosphere.

According to an aspect of the invention, the battery may be manufactured in the same printing process with the remaining components of the sensor and covered by printing or laminating or other relevant process with humidity and salt resistant layer to enable adequate shelf life.

According to an aspect of the invention, a disposable "wet" self-powered sensor may have a hybrid structure, where the battery may be manufactured separately, attached on top of a sensor substrate sheet, e.g. by adhesive, and covered by printing or laminating or other relevant process with humidity and salt resistant layer to enable adequate shelf life.

According to an aspect of the invention, a disposable "wet" self-powered sensor may have a hybrid structure, where the battery may be manufactured separately, encapsulated hermetically with a humidity resistant material, and the hermetically encapsulated battery may be attached on top of an sensor substrate sheet, e.g. by adhesive.

According to an aspect of the invention, a disposable biomedical sensor comprises at least one printed electrode and at least one printed battery provided on a common substrate. The at least one printed battery is sandwiched between humidity-proof material layers on the common substrate sheet.

According to an exemplary embodiment, a substrate is used that is tolerant to humidity and optimized for conductive ink printing. Substrate manufacturers may use chemical treatments for the substrate to assist adhesion to water or solvent based printing and coating systems. This also creates a homogenous printing surface that is humidity tolerant. One example of a possible substrate is double-sided chemically coated polyethylene terephthalate (PET) film.

According to an aspect of the invention a disposable battery is integrated into the sensor by manufacturing it in the same process as the actual electrode. Common printing techniques can be employed, such as silk screen printing, flexography, roll-to-roll, etc. The battery may be covered with humidity and salt resistant layer by printing or laminating or other relevant process.

According to an aspect of the invention, a disposable battery may be manufactured or provided on one side of a substrate while a conductive electrode layer and an associated electrolyte gel may be printed on the opposite side of the substrate.

In exemplary embodiments of the invention, the battery manufactured or provided on the substrate may be covered from the top side (the side away from the substrate) with a humidity and heat resistant dielectric layer. There are several dielectric inks available which are designed for humid conditions. One example of this type of dielectric ink is a UV curing dielectric.

In exemplary embodiments of the invention, the battery manufactured or provided on the substrate may be covered from the top side (the side away from the substrate) with a metal layer (such as aluminum) so as to make the battery humidity and salt resistant. The metal layer may be provided by printing or laminating, for example.

According to an aspect of the invention, the hermetically sealed compartment may be capable of accommodating a pressure of gases created inside the battery during storage, such as by expanding, e.g. swelling, and optionally also during the use of the sensor.

According to an aspect of the invention, the hermetically sealed compartment may comprise removable closure member that can be opened when use of the sensor is started so as to release gases created inside the battery out of the battery. For example, the hermetically sealed compartment may comprise an opening or a gas permeable area closed by said removable member during storage.

According to an aspect of the invention, the hermetically sealed compartment may comprise at least locally a material layer that prevents the humidity and salt to go inside but which enables the gases to get out of the battery and prevents the gas pressure.

In exemplary embodiments of the invention, instead of a dielectric or metal layer, another other humidity resistant material may be used to protect the battery layer, such as glass.

In an exemplary embodiment of the invention, there is also a further humidity resistant layer, such as dielectric layer or a metal layer, manufactured between the substrate and the battery. In another exemplary embodiment, the humidity resistance is provided by the substrate itself, or by any other intermediate layer, and the further special-purpose humidity resistant layer between the substrate and the battery can be omitted.

In an exemplary embodiment of the invention, the top humidity resistant layer and the humidity resistant layer below the battery may be manufactured to join at the surrounding area beyond the periphery of the battery so as to encapsulate the battery into a hermetically sealed compartment or cavity protected from the surrounding humid and saline atmosphere. In exemplary embodiments of the invention, the top humidity resistant layer and the humidity resistant layer below the battery may be sealed together by means of a peripheral seal or layer be manufactured at the surrounding area beyond the periphery of the battery so as to encapsulate the battery into a hermetically sealed compartment protected from the surrounding humid and saline atmosphere.

Figure 3:
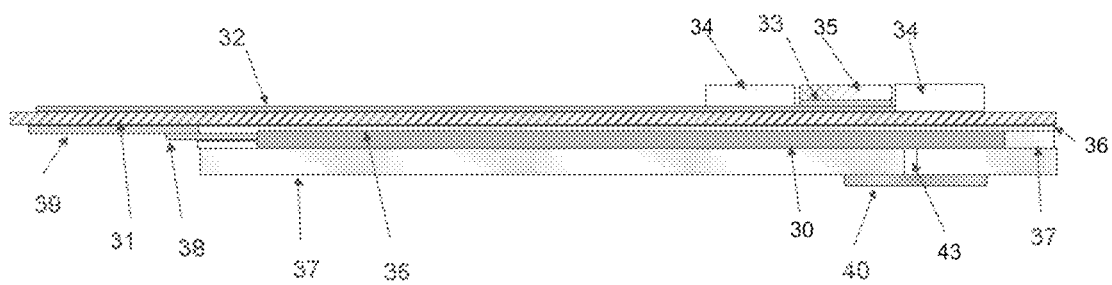
FIG. 3 is a cross-sectional side view of a biomedical self-powered sensor according to an exemplary embodiment.

An illustrating example structure of a biomedical "wet" self-powered sensor which comprises a conductive electrolyte material and withstands a high humidity and saline storage environment is shown in FIG. 3. The exemplary sensor is manufactured on a planar substrate 31 by a printing process, laminating process, or any other process which is suitable for creating material layers, or by a combination of two or more processes. For example, some of the layers may be manufactured by printing and other layers by laminating. The substrate 31 may be made of any suitable substrate material, such as those discussed above with reference to FIGS. 1 and 2.

In the example structure shown in FIG. 3, components of a conventional type of biomedical "wet" sensor may be provided on a first flat surface of the substrate 31. More specifically, a conductive electrode layer 33 (e.g. silver (Ag), silver/silver chloride (Ag/AgCl), a gel element 35 (such as a sponge soaked with a conductive gel) overlaying the conductive electrode 33, and an adhesive member layer 34 (e.g. an adhesive foam material) surrounding the gel element 35 (in the same planar plane) for attaching the electrode to living tissue, for example human forehead or chest, may be manufactured on the first surface of the substrate 31. The surrounding adhesive member 34 may be spaced apart from the gel element 35 so as to block transfer of ions between them. For example, in the case the conductive electrode 33 and the gel element 35 have a circular shape in a plane parallel to the first surface of the substrate 31, the surrounding adhesive member may be ring-shaped such that the inner diameter of the adhesive member is large enough to accommodate the electrode 33 and the gel element 35. The conductive electrode layer 35 may contact the gel element 35 on one side (top side in FIG. 3), and conducting traces 32 (e.g. strips of conductive material) provided on the substrate 31 on the other side. The traces 32 provide electrical connection between the electrode 33 and an associated electronic circuit (such as an electronic circuit 41 in FIG. 4) in the biomedical sensor patch, or via cables to the nearby monitoring device. The traces may be made of Ag or Cu, for example. Although a single electrode is shown in this example, there may be multiple electrodes on the same substrate. An example of a biomedical sensor having multiple electrodes on the same substrate is shown in FIG. 5.

It should be appreciated embodiments of the invention are not intended to be restricted to any specific electrode type but are applicable to any type of biomedical sensor that use any appropriate electrolyte, such as conductive gel, that must be protected from drying and that create a harmful high-humidity environment. Thus, any kind of biomedical "wet" electrode configuration may be provided on the first surface of substrate 31 in place of the configuration shown in FIG. 3.

In the example shown in FIG. 3, a planar printed battery 30 that is encapsulated by a humidity resistant material on the opposite second flat surface of the substrate 31. This configuration minimizes the substrate area required. However, it should be appreciated that the battery may be located on any surface and at any location on the substrate 31. The printed battery 30 may be sandwiched between humidity-proof material layers 36 and 37 on the substrate sheet 31. Although a special-purpose humidity resistant layer 36 located between the substrate 31 and the battery 30, the humidity resistance may be provided by the substrate itself, e.g. by treatment or coating its surface, in which case the special-purpose humidity resistant layer 36 may unnecessary and omitted. There may also be one or more intermediate layers between the humidity resistant layer 36 and the substrate 31.

The battery 30 may be printed or otherwise attached on the humidity resistant layer 36. For example, the battery 30 may be separately manufactured, e.g. commercially available, battery which is attached in a suitable manner, such as with adhesive. The battery 30 may be covered from the top side (the side away from the substrate 31) with the second humidity resistant layer 37, for example by printing or laminating. The humidity resistant layer 37 may be a dielectric layer Or metallic layer, for example. Metal layer may be an aluminum layer or film, for example. The humidity resistant layer 37 may be made of the same or different material as that of the humidity resistant layer 36. In the exemplary embodiment, the top humidity resistant layer 37 and the humidity resistant layer 36 below the battery may be manufactured to join at the surrounding area beyond the periphery of the battery so as to encapsulate the battery 30 into a hermetically sealed compartment (a dry cavity) protected from the surrounding humid and saline atmosphere. Alternatively, the top humidity resistant layer 37 and the humidity resistant layer 36 below the battery may be sealed together by means of a peripheral seal or layer manufactured at the periphery of the battery so as to encapsulate the battery into a hermetically sealed compartment protected from the surrounding humid and saline atmosphere. In the example structure, conductive traces or wires 38 are provided to extend through the humidity resistant encapsulation of the battery 30 so as to provide the supply voltage to an electronic circuit outside the encapsulation (such as an electronic circuit 41 in FIG. 4). Conductive traces 39 may also be provided on the second surface of the substrate 31 to function as supply voltage buses.

In exemplary embodiments of the invention, the hermetically sealed compartment may be capable of accommodating to a pressure of gases created inside the battery during storage. For example, there may be extra space between the battery 30 and the humidity resistant layer 37 to accommodate a small amount of gas. The humidity resistant layer 37 may flexible or otherwise deformable so as to allow expanding, e.g. swelling, of the hermetically sealed battery compartment due to the gases.

In exemplary embodiments, the hermetically sealed compartment may comprise a removable closure member, such as a humidity resistant patch 40. The humidity resistant patch 40 may hermetically seal or close a venting opening, perforation or gas permeable area 43 provided through the humidity resistant layer 37 to the hermetically sealed battery compartment. The venting opening, perforation or gas permeable area 43 may exposed or opened by removing or opening the patch 40 when the use of the sensor is started to release gases created inside the battery out of the battery. This approach may be especially advantageous, when relatively inflexible or rigid humidity resistant layer 37 is employed. The majority of gas formation may happen during the use of battery, and thus the associated problems are alleviated or avoided.

Figure 4:
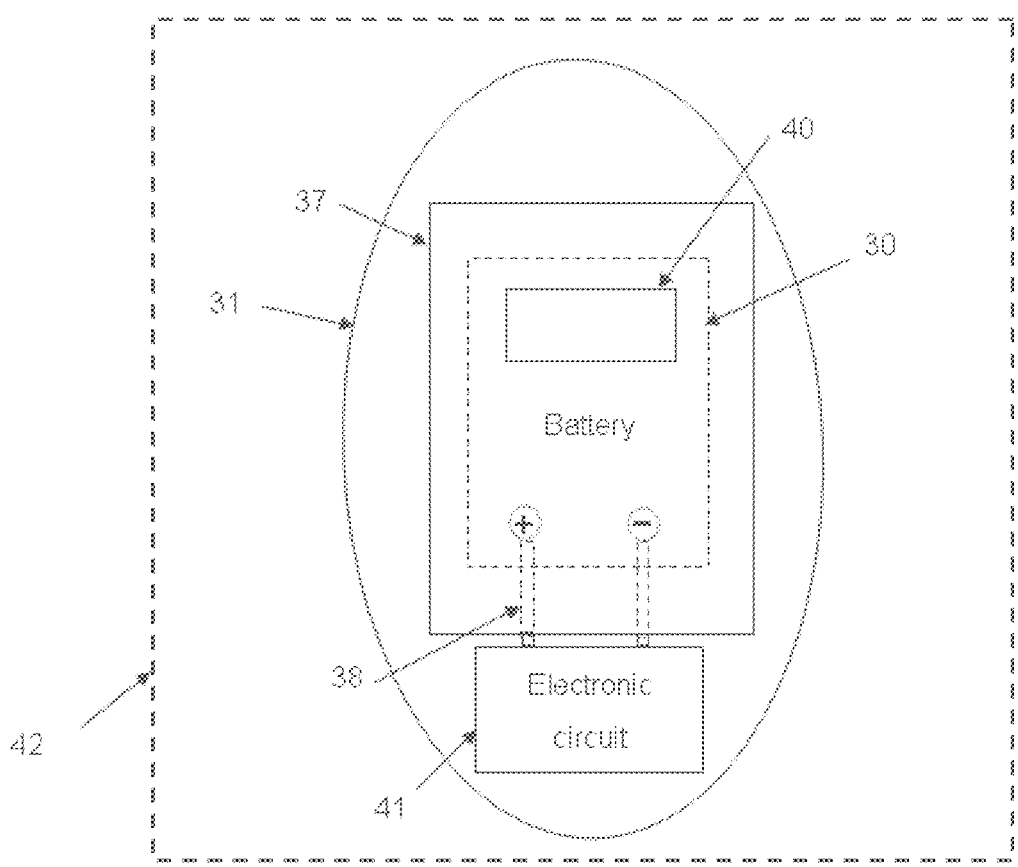
FIG. 4 is a top view of a biomedical self-powered sensor according to an exemplary embodiment.
Figure 5:
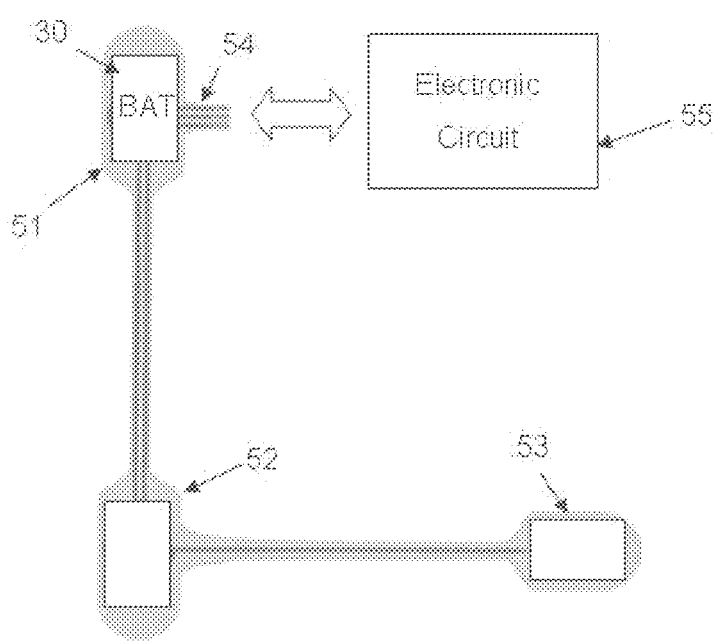
FIG. 5 is a top view of a biomedical self-powered sensor according to an exemplary embodiment.

FIG. 4 is a top view of an exemplary biomedical sensor shown in FIG. 3. In the example shown in FIG. 4 the substrate 31 of the sensor is oval-shaped but it may have any arbitrary shape depending on the application. The battery 30 may be covered by the top humidity resistant layer 37 which extend beyond the periphery of the battery 30, thereby encapsulating the battery 30. The removable closure member, such as a humidity resistant patch 40, may be provided on the top of the layer 37. Conductive traces or wires 38 may extend from the (+) and (−) terminals of the battery 30 through the humidity resistant encapsulation 37 to the electronic circuit(s) 41 outside the encapsulation. Alternatively, the electronic circuit(s) 41 may be within the encapsulation, or remote from the battery.

FIG. 5 is a top view of another exemplary biomedical sensor having multiple (two or more) electrode patches 51, 52, 53. One or more of the electrode patches may be provided with a printed battery 30. The electrode patch 51 may have a connector 54 for connecting a separate electronic circuit 55 to which biosignals and/or the supply voltage from the battery 30 are delivered. The electronic circuit 55 may be reused, while the biomedical sensor with the battery or batteries 30 is disposable single-use product.

Flexible "printable" batteries are commonly available in the markets. For example Enfucell Inc. makes flexible and thin batteries using low cost environmentally friendly materials. The main active components in the batteries are zinc, manganese dioxide and zinc chloride as an electrolyte. When disposed, these batteries require no special treatment, but can be thrown into a normal waste basked together with the electrode. The batteries are manufactured by printing in a roll-to-roll process. SoftBattery® from Enfucell Inc is manufactured with Enfucell allPrinted™ technology. The same or similar technology may be used also then manufacturing the battery 30 on the substrate by printing in the same process with the remaining components of the sensor.

The electronic circuit 42 or 54 may be any electronic circuit associated with the specific biosignal measurement. For example, the electronic circuit may comprise a signal amplifier, a signal processor, a data processor, a data memory, a wireless transmitter, a wireless transceiver, a wired or wireless communication interface, or any combination thereof. For example, the electronic circuit may comprise an ECG-amplifier with body area network connection and operated (e.g. over 24 hours) from the soft battery 30. When the electronic circuit is provided with a wireless transmitter, wireless transceiver, or a wireless communication interface, a self-powered wireless biomedical sensor is achieved. When the electronic circuit is provided with a memory, measured biosignal data may collected and stored in the memory energized by the battery 30 for subsequent downloading to a reading or monitoring device. In other words, a data logger may be provided. The electronic circuit (e.g. an amplifier, memory and/or transmitter) may be either a separate piece of hardware (such as the electronic circuit 55 in FIG. 5), or the electronics may be built to be part of the disposable electrode sheet (such as the electronic circuit 41 in FIG. 4).

In an alternative exemplary embodiment, the battery 30 may be manufactured separately, attached to the humidity resistant layer 36 on the substrate 31, and then covered by the second humidity resistant layer 37 in order to encapsulate the battery 30.

In a still alternative exemplary embodiment, the battery 30 may be manufactured separately, covered by the humidity resistant layers 36 and 37 in order to encapsulate the battery 30, such that the encapsulated battery 30 (with the humidity resistant layers) can be attached on the substrate 31.

In a still alternative exemplary embodiment, the battery 30 may be manufactured separately, the humidity resistant layers 36 and 37 may formed by a package, such as a pouch of humidity resistant material, within which the battery 30 is inserted and sealed in order to hermetically encapsulate the battery 30, such that the package encapsulating the battery 30 can be attached on the substrate 31. The package may be a metallic (e.g. aluminum) pouch similar to a pouch that is used for packaging of biomedical "wet" electrodes. Suitable traces or wires 38 may be taken out of the encapsulated battery to provide the supply voltage to an external electronic circuit (such as circuit 41 in FIG. 4). The resulting hybrid structure may result in a similar arrangement as shown in FIGS. 3 and 4, the reference numerals 36 and 37 depicting the package or pouch of the battery 30.

Exemplary embodiments of the invention allows storing of a disposable self-powered sensor within an enclosure or a package which provides a proper atmosphere to prevent the drying of the electrolyte and prolong the shelf life of the sensors. For example, diagnostic quality ECG sensors can be stored in the same pouch with the soft battery. In FIG. 4, the dash line 42 depicts a hermetic package or pouch for storing the biomedical sensor provided with a soft battery.

Embodiments of the invention provide various advantages. A disposable power source (with capacity for operation over a required monitoring period, such as 24 hours) on a biomedical sensor is a perfect fit with hospital's logistics and care process. Infection control in hospitals is improved. No extra work from maintaining or special handling of the batteries of wireless sensors (e.g. recycling) is needed. Use of wireless sensors reduces the cable clutter in the hospital. A low cost highly integrated solution is enabled.

This written description uses examples to disclose the invention, including the best mode, and also to enable any skilled person to make and use the invention. The patentable scope of the invention is defined by the claims, and may include other examples that occur to those skilled in the art. Such other examples are intended to be within the scope of the claims if the have structural elements that do not differ from the literal language of the claims, or if they include equivalent structural elements with insubstantial differences from the literal language of the claims.

What is claimed is:

1. A biomedical sensor, comprising:
    a substrate sheet;
    at least one electrode printed directly on a first surface of the substrate sheet, the at least one electrode being provided with an electrolyte element to enhance electrical contact with a surface to be measured;
    a hermetically sealed compartment disposed on a second surface of the substrate sheet;
    at least one printable soft battery disposed within the hermetically sealed compartment, the hermetically sealed compartment comprising:
        a first humidity-proof material layer between the second surface of the substrate sheet and the battery; and
        a second humidity-proof material layer on a side of the battery opposite the second surface of the substrate sheet;
    the biomedical sensor further comprising a venting opening extending through the second humidity proof material layer of the hermetically sealed compartment; and
    a removable humidity resistant patch over the venting opening.

2. A biomedical sensor according to claim 1, wherein one of the first humidity-proof material layer and the second humidity-proof material layer comprises the substrate sheet itself made of humidity-proof material or chemically treated to be humidity-proof.

3. A biomedical sensor according to claim 1, wherein one of the first humidity-proof material layer and second humidity-proof material layer comprises a humidity-proof material layer covering a top of the printed soft battery.

4. A biomedical sensor according to claim 1 wherein at least one of the first humidity-proof material layer and the second humidity-proof material layer comprises a metal layer or a dielectric layer.

5. A biomedical sensor according to claim 1, wherein the soft battery is manufactured in the same printing process with the remaining components of the electrode and covered by printing or laminating or other relevant process with a humidity-proof layer.

6. A biomedical sensor according to claim 1, wherein the soft battery is manufactured separately, attached on top of an electrode substrate sheet, and covered by printing or laminating or other relevant process with a humidity-proof layer.

7. A biomedical sensor according to claim 1, wherein the soft battery is manufactured separately, encapsulated hermetically with a humidity resistant material, and the hermetically encapsulated soft battery is attached on top of an electrode substrate sheet.

8. A biomedical sensor according to claim 1, wherein the hermetically sealed compartment comprises one or more of the following characteristics:
   the hermetically sealed compartment is capable of accommodating to a pressure of gases created inside the soft battery during one or more of storage or use of the sensor; or
   the hermetically sealed compartment comprises a gas permeable area closed by the removable closure member during storage, the removable closure member being opened when use of the sensor is started so as to vent out gases created inside the soft battery through the gas permeable area.

9. A biomedical sensor according to claim 1, comprising an electronic circuit energized from the soft battery.

10. A biomedical sensor according to claim 9, wherein the electronic circuit is configured for wireless transmission of biomedical measurement data.

11. A biomedical sensor according to claim 9, wherein the electronic circuit is configured to store biomedical measurement data.

12. A biomedical sensor according to claim 9, wherein the electronic circuit is configured to process biomedical measurement data.

13. A hermitically sealed package containing a biomedical sensor, the biomedical sensor further comprising:
   a substrate sheet;
   at least one electrode printed directly on a first surface of the substrate sheet, the at least one electrode being provided with an electrolyte element to enhance electrical contact with a surface to be measured; and
   a hermetically sealed compartment disposed on a second surface of the substrate sheet;
   at least one printable soft battery disposed within the hermetically sealed compartment, the hermetically sealed compartment comprising:
      a first humidity-proof material layer between the second surface of the substrate sheet and the battery; and
      a second humidity-proof material layer on a side of the battery opposite the second surface of the substrate sheet;
   the biomedical sensor further comprising a venting opening extending through the second humidity proof material layer of the hermetically sealed compartment; and
   a removable humidity resistant patch over the venting opening.

14. A hermitically sealed package according to claim 13, wherein the package is a pouch made of aluminum foil.

15. A hermitically sealed package according to claim 13, wherein the soft battery is manufactured in the same printing process with the remaining components of the electrode and covered by printing or laminating or other relevant process with a humidity-proof layer.

16. A hermitically sealed package according to claim 13, wherein the soft battery is manufactured separately, attached on top of an electrode substrate sheet, and covered by printing or laminating or other relevant process with a humidity-proof layer.

17. A hermitically sealed package according to claim 13, wherein the soft battery is manufactured separately, encapsulated hermetically with a humidity resistant material, and the hermetically encapsulated soft battery is attached on top of an electrode substrate sheet.

18. A hermitically sealed package according to claim 1, wherein the hermetically sealed compartment is capable of accommodating to a pressure of gases created inside the soft battery during storage, and/or during use of the sensor.

19. A hermitically sealed package according to claim 13, wherein the hermetically sealed compartment comprises a gas permeable area closed by the removable closure member during storage, the removable closure member being opened when use of the sensor is started so as to vent out gases created inside the soft battery through the opening or a gas permeable area.

* * * * *